(12) United States Patent
Wang et al.

(10) Patent No.: US 8,932,863 B2
(45) Date of Patent: Jan. 13, 2015

(54) METHODS FOR EVALUATING FUEL COMPOSITIONS

(75) Inventors: Haiyan Wang, Hoffman Estates, IL (US); Michael J. McCall, Geneva (IL)

(73) Assignee: UOP LLC, Des Plaines, IL (US)

( * ) Notice: Subject to any disclaimer, the term of this patent is extended or adjusted under 35 U.S.C. 154(b) by 553 days.

(21) Appl. No.: 13/327,565

(22) Filed: Dec. 15, 2011

(65) Prior Publication Data

US 2013/0153759 A1  Jun. 20, 2013

(51) Int. Cl.
  *G01N 33/22* (2006.01)
  *H01J 49/26* (2006.01)
(52) U.S. Cl.
  USPC ............... 436/60; 436/71; 436/173; 436/179; 250/282
(58) Field of Classification Search
  USPC ............... 436/60, 71, 173, 174, 179; 250/282
  See application file for complete search history.

(56) References Cited

U.S. PATENT DOCUMENTS

| | | | |
|---|---|---|---|
| 5,452,232 | A | 9/1995 | Espinosa et al. |
| 5,504,259 | A | 4/1996 | Diebold et al. |
| 6,175,111 | B1 | 1/2001 | Sorita et al. |
| 6,180,845 | B1 | 1/2001 | Catallo et al. |
| 2010/0211329 | A1* | 8/2010 | Farquharson et al. ......... 702/28 |
| 2011/0223672 | A1 | 9/2011 | Tumiatti et al. |

FOREIGN PATENT DOCUMENTS

| | | |
|---|---|---|
| RU | 2149887 C1 | 5/2000 |
| SU | 1065349 A | 1/1984 |
| SU | 1201772 A | 12/1985 |
| WO | 9300415 A1 | 1/1993 |
| WO | 2004/002309 A2 | 3/2004 |
| WO | 2009082418 A2 | 7/2009 |

OTHER PUBLICATIONS

Eide et al. Energy and Fuels, vol. 21, 2007, pp. 3702-3708.*
Abnisa, Faisal, et al., "Optimization and characterization studies on bio-oil production from palm shell by pyrolysis using response surface methodology," Biomass and Bioenergy, vol. 35, No. 8, p. 3604-3616, Aug. 2011.
Wang, Shurong, et al., "Influence of the interaction of components on the pyrolysis behavior of biomass," Journal of Analytical and Applied Pyrolysis, vol. 91, No. 1, p. 183-189, May 2011.
Simonsick, W.J., Jr., et al., "The characterization of novel dispersants, fluorinated surfactants, and modified natural oils by laser desorption Fourier transform ion cyclotron resonance mass spectrometry," International Journal of Mass Spectrometry and Ion Processes, vol. 157-158, p. 379-390, Dec. 20, 1996.
Wu, Z., "Compositional analysis of complex organic mixtures by electrospray ionization Fourier transform ion cyclotron resonance mass spectroscopy," Florida State University, Dissertation, 2004.
Schaub, T.M., et al., "Instrumentation and method for ultrahigh resolution field desorption ionization fourier transform ion cyclotron resonance mass spectrometry of nonpolar species," Analytical Chemistry, vol. 77, No. 5, p. 1317-1324, Mar. 1, 2005.
Fard, Ahmad Mokhtari, et al., "High-resolution electrospray-ionization Fourier-transform ion cyclotron resonance and gas chromatography-mass spectrometry of macadamia nut oil," Australian Journal of Chemistry, vol. 56, No. 5, p. 499-508, 2003.
Agblevor, F.A., et al., "Pyrolytic analysis and catalytic upgrading of lignocellulsoic materials by molecular beam mass spectrometry," IGT 16th Annual "Energy from Biomass and Wastes" Conference (Orlando, FL Mar. 2-6, 1992) [Proceedings] 767-95 (1993), Mar. 2, 1992.

\* cited by examiner

*Primary Examiner* — Maureen Wallenhorst

(57) ABSTRACT

Methods for evaluating a fuel are provided. In one embodiment, a method of evaluating a fuel includes providing a testing specimen of the fuel. Also, the method includes analyzing the testing specimen and identifying a compound in the testing specimen. The method also provides for determining the fuel is biologically-sourced based on the identified trace compound.

19 Claims, 3 Drawing Sheets

METHODS FOR EVALUATING FUEL COMPOSITIONS

TECHNICAL FIELD

The present invention generally relates to methods for evaluating fuel compositions, and more particularly relates to methods for evaluating fuels to identify a trace compound or compounds therein, and to determine a characteristic of the fuel based on the identified compound.

BACKGROUND

As the demand for fuels such as aviation fuel increases worldwide there is increasing interest in feedstock sources other than petroleum crude oil for producing the fuel. One such source is what has been termed biological feedstocks. These renewable biological feedstocks include, but are not limited to, plant oils such as corn, jatropha, camelina, rapeseed, canola, soybean and algal oils, animal fats such as tallow, and fish oils. A common feature of these feedstocks is that they are composed of mono- di- and tri-glycerides, and free fatty acids (FAA). The aliphatic carbon chains in the glycerides and FFAs can be saturated or mono-, di- or poly-unsaturated. Most of the glycerides in the renewable feed stocks will be tri-glycerides, but some of the glycerides in the renewable feedstock may be mono-glycerides or di-glycerides. The amount and distribution of compounds such as glycerides may differ between, and be indicative of, biological feedstocks. Biologically-sourced fuel, i.e., fuel that is formulated from the processing of renewable biological feedstock typically retains trace compounds, such as glycerides or FAA, that are not found in petroleum-derived fuels.

Further, all fuels typically retain trace components characteristic of their feed source after processing. Typically, these trace components usually do not affect the bulk fuel properties. For instance, conventional jet fuels may retain trace levels of sulfur and nitrogen heteroatoms characteristic of the oil field or source of the feedstock. Further, these trace components are typically present only in trace levels (i.e., low ppm levels or less) in the processed fuel, and are not easily discernable by standard analytical methods.

While biologically-sourced fuels are generally considered to be more environmentally friendly than petroleum-derived fuels, there are differences in desirability among biologically-sourced fuels depending on the source of the fuel's feedstock. For instance, there may be little demand for biologically-sourced fuels created from plants harvested from protected lands or from ecologically fragile areas or areas of environmental significance. For example, biologically-sourced fuel formulated from palm oil produced as a result of rain forest deforestation is disfavored. Other disfavored biologically-sourced fuels include those formed from food crops, as the use of food crops for fuel causes food price inflation, the diversion of farm land away from food crops to energy crops, or even food shortages. Thus, a potential fuel purchaser may wish to determine the fuel's feedstock before purchase so as to determine if the fuel is from a biologically-sourced feedstock and to discourage production of fuel from undesirable feedstock.

Several biologically-sourced fuels are easily discernable from other fuels, such as petroleum-derived fuels, because they contain compounds having at least one oxygen atom that are present in percent levels in the final blended fuel. Examples include ethanol blended in petroleum-derived gasoline and fatty-acid methyl esters (FAME)—or biodiesel—blended in petroleum-derived diesel. In each of these cases, the ethanol is easily identified from the gasoline in the gasoline blend, and the FAME is easily identified from diesel in the diesel blend.

Other biological-sourced fuels are not easily discernable from petroleum-derived fuels because they are mostly composed of the same components as the petroleum-derived fuel. One example is renewable diesel—or green diesel—a product formed from complete hydrogenation and deoxygenation of biological feedstocks predominantly composed of glycerides and free fatty acids. Green diesel contains mostly paraffins that are not easily distinguished from petroleum-derived paraffins. Another example is Hydrotreated renewable jet fuel (HRJ), also known as green jet fuel, and also known as hydroprocessed esters and free fatty acids (HEFA). This fuel is also produced by complete hydrogenation and deoxygenation of biological feedstocks predominantly composed of glycerides and free fatty acids, but the paraffin product is further processed to produce paraffins in the kerosene range as a drop-in blend for aviation fuel. These biologically-derived paraffins are not easily distinguished from petroleum-derived paraffins.

Accordingly, it is desirable to provide methods for evaluating a fuel to certify that the fuel is biologically-sourced. Further, it is desirable to provide methods for evaluating a fuel to discern a specific feedstock as the source for the fuel. Also, it is desirable to provide methods for evaluating a fuel to determine a characteristic of the fuel based on the identification of trace compounds identified within the fuel when the biological-sourced fuel contains major components indistinguishable from petroleum-derived components. Further, it is desirable to identify these trace compounds when present in only high parts per billion (ppb) to low parts per million (ppm) concentrations. Furthermore, other desirable features and characteristics will become apparent from the subsequent detailed description and the appended claims, taken in conjunction with the accompanying drawings and the foregoing technical field and background.

BRIEF SUMMARY

Methods for evaluating a fuel are provided by identifying trace components in the fuel. In accordance with an exemplary embodiment, a method of evaluating a fuel includes providing a testing specimen of the fuel. Also, the method includes analyzing the testing specimen and identifying a trace compound in the testing specimen. The method also provides for determining the fuel is biologically-sourced based on the identified trace compound.

In accordance with another exemplary embodiment, a method of evaluating a fuel includes analyzing the fuel to identify a compound therein. The method also includes determining that at least a portion of the fuel is biologically-sourced based on the identified trace compound.

In accordance with another exemplary embodiment, a method of evaluating an aviation fuel includes enhancing a trace compound in the aviation fuel for analysis. The method further provides for analyzing the fuel to identify the trace compound in the fuel. The method provides for discerning a feedstock as a source for the fuel based on the identified trace compound.

BRIEF DESCRIPTION OF THE DRAWINGS

The methods for evaluating fuel will hereinafter be described in conjunction with the following drawing figures, wherein like numerals denote like elements, and wherein.

DETAILED DESCRIPTION

The following Detailed Description is merely exemplary in nature and is not intended to limit the methods of evaluating fuels. Furthermore, there is no intention to be bound by any expressed or implied theory presented in the preceding technical field, background or brief summary, or in the following detailed description.

Various methods for evaluating fuel compositions are provided herein. Specifically, the methods can be employed to identify a compound in the fuel and, based on the identified compound, (a) determine whether the fuel is biologically-sourced, i.e., whether its feedstock is biomass; (b) determine the source of the specific feedstock, e.g., corn oil, jatropha oil, camelina oil, rapeseed oil, canola oil, soybean oil, algal oil, animal fats, fish oil or the like; (c) identify a compound in the feedstock; and/or (c) thus, determine a fuel property characteristic due to presence of the compound.

Figure 1:
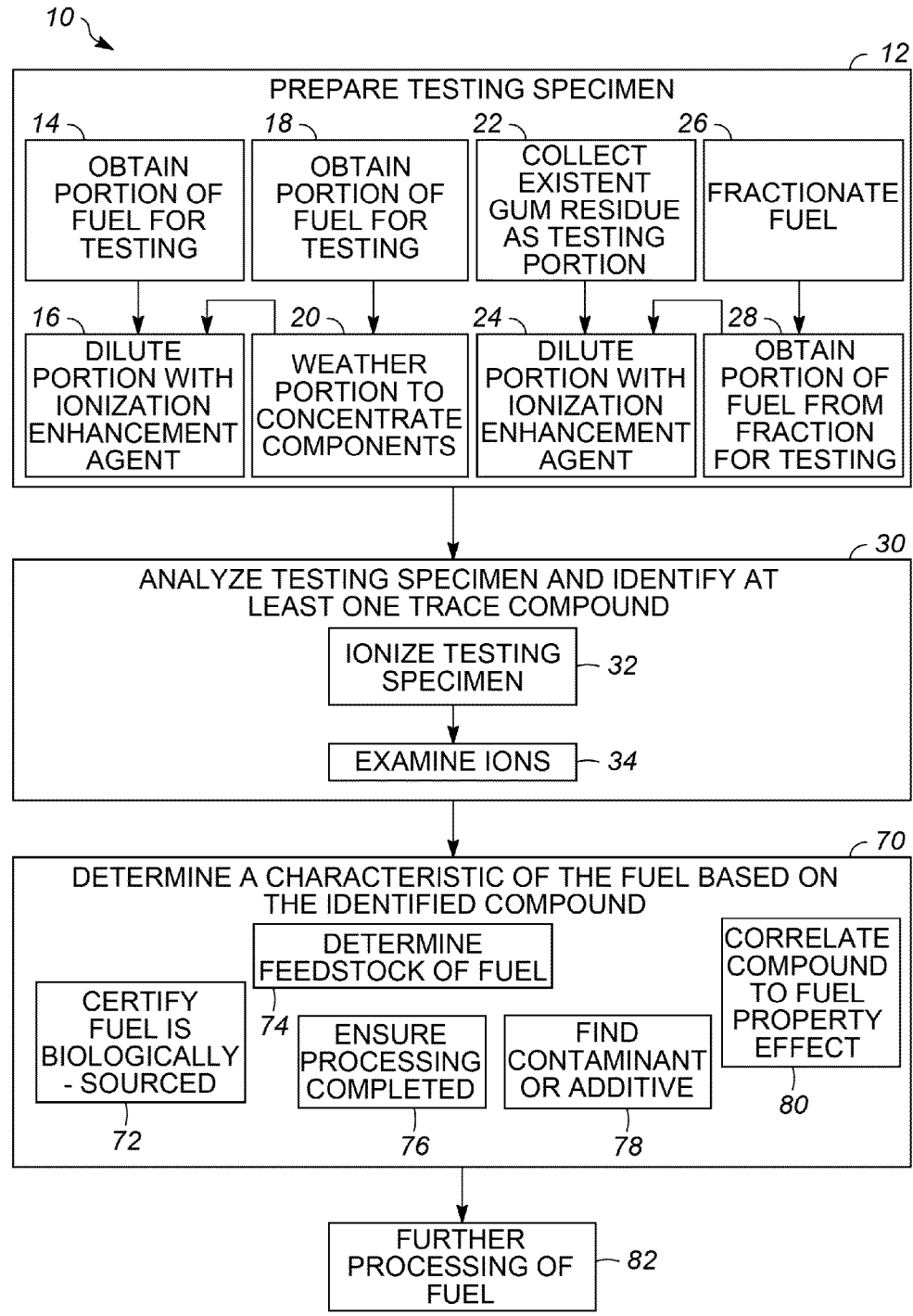
FIG. 1 is a flow chart illustrating methods for evaluating a fuel in accordance with various embodiments herein.
Figure 2A:
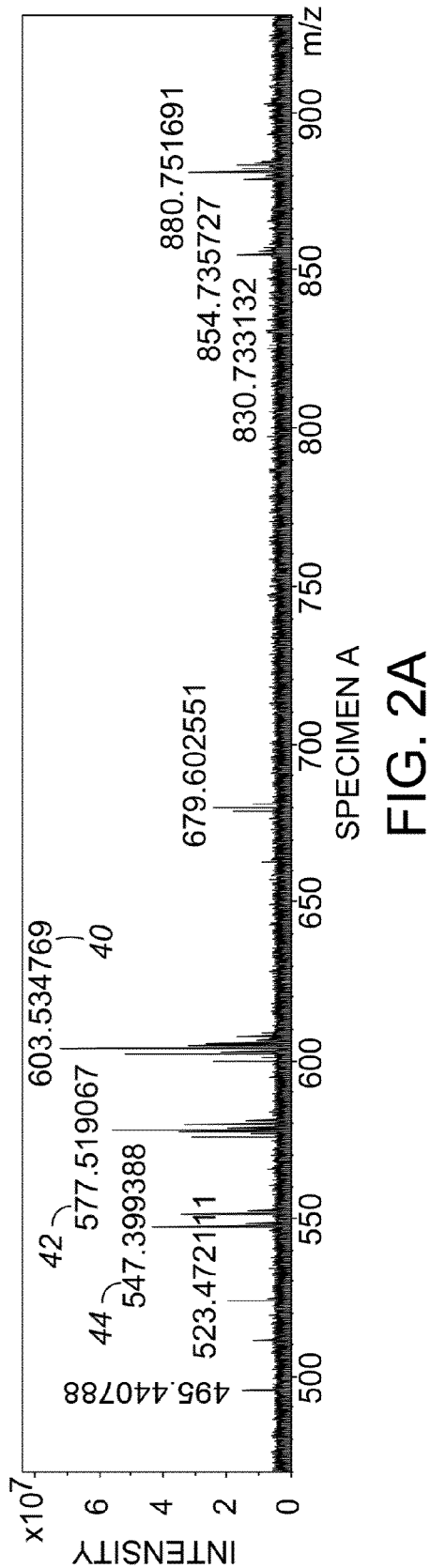
FIGS. 2A-2D are spectrometry graphs of four testing specimens in accordance with various embodiments herein.
Figure 2B:
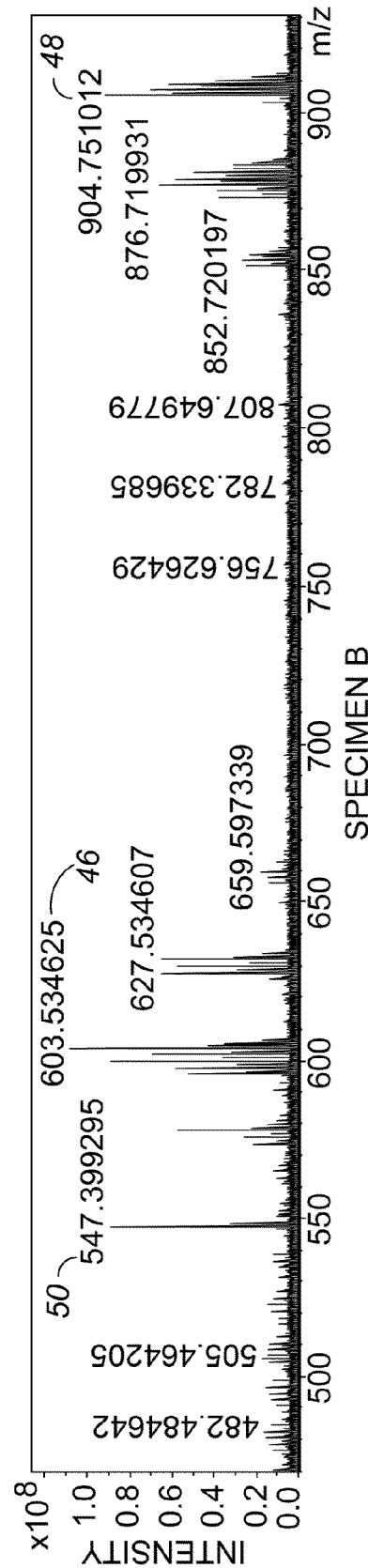
Figure 2C:
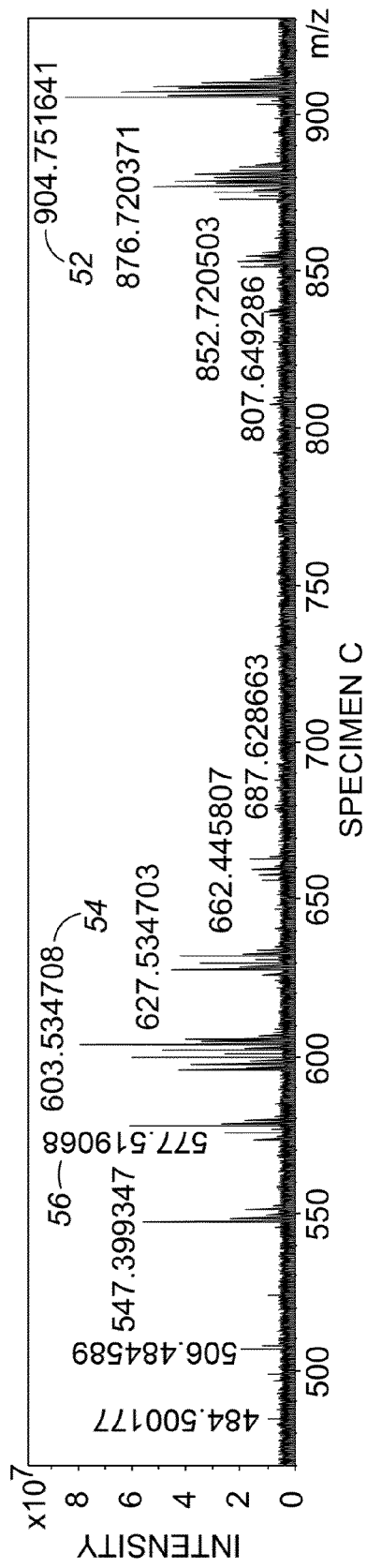
Figure 2D:
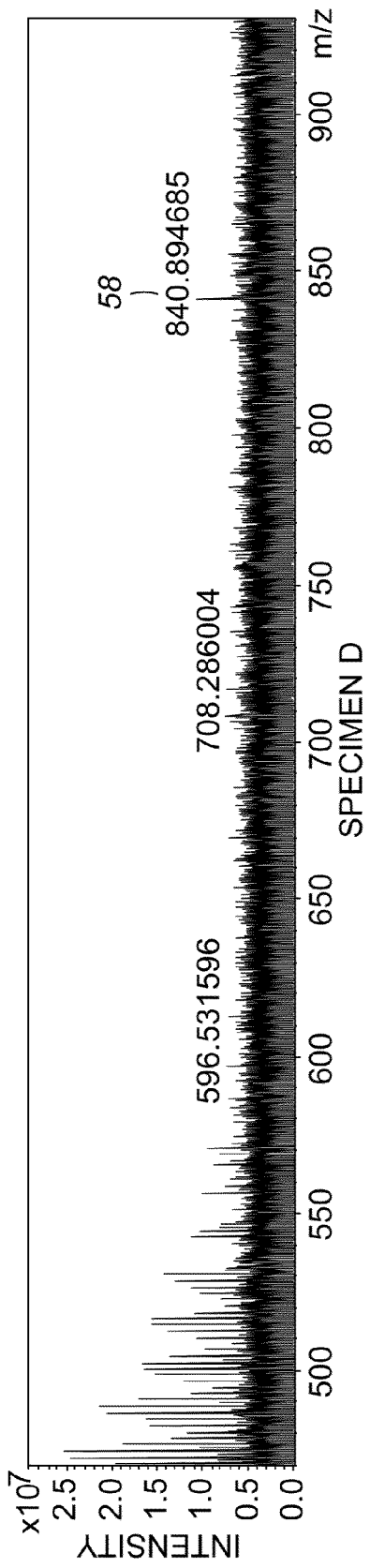

In accordance with an exemplary embodiment, FIG. 1 illustrates a method 10 for evaluating a fuel to determine a selected characteristic of the fuel. As used herein, a "selected characteristic" of the fuel includes whether the fuel is biologically-sourced, the source of the feedstock for the fuel, the identity of a compound in the fuel, or a fuel property characteristic due to presence of the identified compound in the fuel.

PREPARATION OF TESTING SPECIMEN. The method 10 begins by providing a testing specimen from the fuel (step 12). The testing specimen can be provided through preparation by several different processes. A first embodiment includes obtaining a portion of fuel for testing (step 14). For example, a selected volume of fuel is isolated for testing. The portion is then diluted with an ionization enhancement agent (step 16). In an exemplary embodiment, the ionization enhancement agent is toluene, and the portion is diluted at a ratio of 1:1. As discussed below, the ionization enhancement agent enhances certain fuel components for testing by promoting the ionization of polar species within the testing portion, including trace compounds. Other ionization enhancement agents include, without limitation, anisole, quinoline, and xylenes. As used herein, "trace compounds" are those present at levels equal to or less than 100 ppm of the fuel.

In FIG. 1, a second embodiment for preparing the testing specimen also includes obtaining a portion of fuel for testing (step 18). The portion is then weathered to concentrate components of the fuel (step 20). For example, the portion may be weathered under a nitrogen atmosphere at an elevated temperature (about 80° C. to about 100° C.). Alternatively, the portion may be weathered at lower or ambient temperatures under sub-atmospheric pressure. In certain embodiments, the weathering action removes the light end of the fuel (for example, fuel components having boiling points below 300° C.) and concentrates the heavy end of the fuel (for example, fuel components having boiling points above 300° C., i.e., higher than kerosene range, as defined in D1655 table 1). As shown in FIG. 1, the concentrated components may be optionally diluted with the ionization enhancement agent (step 16) to complete preparation of the testing specimen. In an exemplary embodiment, the ionization enhancement agent is toluene, and the portion is diluted at a ratio of 1:1.

In a third embodiment for preparing the testing specimen, existent gum residue is collected as the testing portion (step 22). The existent gum residue is created according to the standard method for testing gum content in fuels by jet evaporation (ASTM Test Method D381 or IP540). In the standard method, 50±0.5 mL of aviation fuel is evaporated under controlled conditions of temperature and flow of steam. A residue results and is weighed under the method to determine gum content. In an embodiment herein, the gum residue is collected by washing with about 1 mL of a solvent, for example, carbon disulfide and/or dichloromethane, to form a residue solution as the testing portion. This testing portion is then diluted with an ionization enhancement agent (step 24). In an exemplary embodiment, the ionization enhancement agent is toluene, and the portion is diluted at a ratio of 1:1.

In another embodiment for preparing the testing specimen, the fuel is fractionated into at least two cuts (step 26). For example, the fuel may be fractionated into a light cut having an initial boiling point less than 300° C. and a heavy cut having an initial boiling point greater than 300° C. Fractionation is performed under a vacuum to avoid air oxidation of components in the fuel. In an exemplary embodiment, fractionation is performed by the known spinning band distillation process. As shown, a portion of the fractionated fuel is then selected and obtained for testing (step 28). Typically, the heavy cut holds compounds of interest for biologically-sourced fuel and is selected as the testing portion. The portion optionally may be diluted with the ionization enhancement agent (step 24). In an exemplary embodiment, the ionization enhancement agent is toluene, and the portion is diluted at a ratio of 1:1. It will be appreciated that steps 26 and 28 may be reversed in order, i.e., the testing portion may first be isolated from the fuel and then fractionated, before the optional dilution of the selected cut (step 24).

ANALYSIS OF TESTING SPECIMEN. The method continues after the preparation of the testing specimen (step 12) with the analysis of the testing specimen to identify at least one compound (step 30). In an exemplary embodiment, analysis of the testing specimen includes ionizing the testing specimen (step 32). In an exemplary embodiment, chemicals of interest in the testing specimen are ionized by an atmospheric pressure photoionization (APPI) source. The APPI source is able to ionize polar species such as cycloparaffins, aromatics, oxygenates, thiophenes and nitrogen compounds, but does not ionize non-polar species. Therefore, normal and iso-alkanes cannot be ionized by APPI and accordingly, are not identified during analysis. In an exemplary embodiment, the APPI source nebulizes components in the testing specimen at a feed rate of about 200 µL/hr, and the APPI nebulizer temperature is about 350° C. While the exemplary embodiment utilizes APPI, other methods of ionization can be used, including electrospraying, matrix assisted laser desorption ionization, electron impact, and chemical ionization.

After ionization, the resulting ions are examined (step 34). In an exemplary embodiment, examination is performed by Fourier transform ion cyclotron resonance mass spectrometry (FT-ICR MS), which is a high resolution mass spectrometric (HRMS) technique. The spectrometry technique measures ions by detecting their cyclotron frequencies in a cell that is located inside a magnetic field. Due to its ultra-high mass resolution, mass accuracy and sensitivity, FT-ICR MS is able to determine the molecular formula of individual chemicals existing in a complex organic mixture. As realized herein, detection of trace levels of impurities and/or contaminants in a complex matrix such as fuels is possible through the examination (step 34). While detection of many trace compounds is possible, the spectrometry technique is not a quantitative technique and sensitivity for molecules less than 200 amu is lower compared to heavier species. In addition, isomers cannot be distinguished. Further, proposed structural identification of compounds is based on known process chemistry. In exemplary embodiments, during examination, mass spectra are obtained over the mass range of about 125 to about 2,000 amu. In an exemplary embodiment, the examination includes a series of 300 transients of 4 MW data points that are summed and Fourier transformed for each spectrum. This results in a mass resolution of approximately 320,000 at mass 400 amu. Further, the toluene background is checked between testing specimens to assure that there is no cross contamination. The raw data resulting from the spectrometry technique is then calibrated and processed to identify at least one compound of interest.

FIG. 2 shows the graphical analysis results for four testing specimens, from top to bottom: Specimen A, Specimen B, Specimen C and Specimen D. Specimens A-C are biologically-sourced, while Specimen D is a petroleum-derived fuel. As shown in FIG. 2, Specimen A includes its greatest peaks at 603.534769 m/z (labeled 40), 577.519067 m/z (labeled 42), and at 547.399388 m/z (labeled 44). Further, Specimen B has its greatest peaks at 603.534625 m/z (labeled 46), 904.751012 m/z (labeled 48), and 547.399295 m/z (labeled 50). Specimen C has its greatest peaks at 904.751641 m/z (labeled 52), 603.534708 m/z (labeled 54), and 577.519068 m/z (labeled 56). Specimen D has only one distinguishable peak above 600 m/z, at 840.894685 m/z (labeled 58). While peaks 40-58 are identified and labeled in FIG. 2, it will be appreciated that each peak resulting from spectrometry analysis can be used to identify compounds found in a testing specimen.

In FIG. 2, one or more distinguishing compounds may be identified from the spectrometry results. The peaks in the range of about 500 m/z to about 650 m/z exhibited by Specimens A-C indicate the presence of di-glycerides in the testing specimens. Further, the peaks of about 850 m/z to about 1000 m/z exhibited by Specimens A-C indicate the presence of tri-glycerides in the testing specimens. As illustrated in FIG. 2, the graph for the petroleum-derived fuel Specimen D does not indicate the presence of any glycerides. In addition or alternatively to the di-glycerides and tri-glycerides, other compounds that may distinguish a biologically-sourced fuel include mono-glycerides, squalene, and cholesterol. Further, the distinguishing compound may include distinct contaminants that are unique to a feedstock, or even a feedstock from a specific geographic location, and its resulting fuel. Contaminants may also be indicative of storage tanks or the use of additives. In exemplary embodiments, compounds may be identified through comparison to analysis results for samples of known compositions or through comparison to a library of known compositions.

DETERMINING CHARACTERISTIC OF FUEL. Referring back to FIG. 1, the method includes determining a characteristic of the fuel based on the identified compound (step 70). For example, it may be determined from the identification of glycerides in Specimens A-C, that Specimens A-C are from biological feedstock because glycerides are present in biologically-sourced fuels, but not in petroleum-derived fuels. Thus, the characteristic of being biologically-sourced is determined (step 72). It will be appreciated that a fuel specimen may be determined to be partially biologically-sourced based on the quantity of identified compounds indicative of a biological source, and/or the presence of identified compounds indicative of petroleum-derived fuels.

Also, in an exemplary embodiment, a specific compound can be identified from the fuel analysis and can allow determination of the feedstock (step 74). For example, soy beans are known to include a high percentage of unsaponifiables (or steroid/cholesterol analogs). Therefore, the identification of an unsaponifiable compound or compounds can allow the determination that the fuel was formulated, at least partially, from a soy bean feedstock.

In accordance with another embodiment, the identification of the trace compound, or absence of a trace compound, can be used to certify or ensure that adequate processing, e.g., deoxygenation, was completed during formulation of the fuel (step 76). Also, the characteristic may be the presence of a trace contaminant or additive, and the method can include finding such a trace contaminant or additive (step 78).

Occasionally, the presence of a trace compound or compounds may affect the properties of the fuel, for example, the dosing of the wrong additive or additive concentration. In an exemplary embodiment, the identified compound or compounds may be correlated to a fuel property effect (step 80). As used herein, "fuel property effect" is a result or effect the fuel may have on systems that burn the fuel for energy or otherwise come in contact with the fuel due to presence of the identified compound. For example, the analysis of the fuel may indicate the presence of heavy species such as trace heavy alkylaromatics. Such heavies may cause cold temperature ignition plugging problems under certain process conditions and injector designs. Thus, the presence of the heavy species may be correlated to the fuel property effect (plugging). Once the identified compound is correlated to a fuel property effect, the effect can be accentuated, minimized, eliminated, or the like by further processing of the fuel. (step 82). For example, the fuel may be further processed to decrease or eliminate the trace heavies, thus minimizing or eliminating the cold temperature ignition plugging problems caused by the trace heavy alkylaromatics. Likewise, further processing can be used to eliminate contaminates or additives located in step 78, or to complete processing if indicated that processing was not completed in step 76.

Accordingly, the evaluation methods described herein can be used to determine the presence of certain compounds in the fuel during testing specimen preparation, to identify those compounds during analysis of the fuel, and to determine a characteristic of the fuel based on the identified compound or compounds. In addition, the methods herein can be useful in the qualification and certification of new fuels, in monitoring production quality, or to quantify the renewable content of a fuel. Further, the methods herein may be used in troubleshooting when problematic performance of the fuel is due to fuel property effects caused by the presence of certain compounds, even in trace amounts.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the processes without departing from the scope defined by the claims, which includes known equivalents and foreseeable equivalents at the time of filing this patent application

What is claimed is:

1. A method of determining whether or not a fuel is biologically-sourced comprising:
   obtaining a portion of the fuel;
   diluting the portion of the fuel with an ionization enhancement agent to form a testing specimen of the fuel;
   analyzing the testing specimen;

identifying a trace compound in the testing specimen, wherein the trace compound is present in an amount equal to or less than 100 ppm; and determining if the fuel is biologically-sourced based on the identified trace compound.

2. The method of claim 1 wherein identifying comprises identifying a biologically-sourced trace compound, wherein the biologically-sourced trace compound is chosen from the group consisting of mono-glycerides, di-glycerides, tri-glycerides, squalene, and cholesterol.

3. The method of claim 1 further comprising identifying a feedstock as a source for the fuel based on the identified trace compound.

4. The method of claim 1 further comprising correlating the identified trace compound to a fuel property effect.

5. The method of claim 4 further comprising processing the fuel to reduce the identified trace compound.

6. The method of claim 1 wherein the identified trace compound is a contaminant, and further comprising ascertaining the source of the contaminant based on the identified trace compound.

7. The method of claim 1 further comprising weathering the portion of the fuel before diluting the portion of the fuel.

8. The method of claim 1 further comprising fractionating the fuel to obtain the portion of the fuel for use as the testing specimen.

9. The method of claim 1 wherein a portion of the fuel comprises collecting existent gum residue from the fuel.

10. The method of claim 1 wherein analyzing comprises:
ionizing the testing sample to form ions; and
examining the ions with a high resolution mass spectrometric technique to identify the trace compound.

11. The method of claim 1 wherein analyzing comprises:
ionizing the testing sample to form ions; and
examining the ions with a Fourier transform ion cyclotron resonance mass spectrometric technique to identify the trace compound.

12. A method of determining whether or not a fuel is biologically-sourced comprising:
obtaining a testing specimen of the fuel, wherein the testing specimen includes an organic mixture of chemicals;

analyzing the testing specimen of the fuel to identify the molecular formula of individual chemicals in the organic mixture; and determining if at least a portion of the fuel is biologically-sourced based on the identified molecular formula of individual chemicals.

13. The method of claim 12 further comprising identifying a feedstock as a source for the testing specimen of the fuel based on the identified molecular formula of individual chemicals.

14. The method of claim 12 wherein analyzing comprises identifying a biologically-sourced compound, wherein the biologically-sourced compound is chosen from the group consisting of mono-glycerides, di-glycerides, tri-glycerides, squalene, and cholesterol.

15. The method of claim 12 wherein analyzing comprises:
ionizing the testing specimen of the fuel to form ions; and
examining the ions with a high resolution mass spectrometric technique to identify the molecular formula of individual chemicals in the organic mixture.

16. The method of claim 12 wherein analyzing comprises:
ionizing the testing specimen of the fuel to form ions; and
examining the ions with a Fourier transform ion cyclotron resonance mass spectrometric technique to identify the molecular formula of individual chemicals in the organic mixture.

17. A method of evaluating an aviation fuel comprising:
collecting existent gum residue from the aviation fuel;
enhancing a trace compound in the existent gum residue from the aviation fuel for analysis;
analyzing the existent gum residue of the aviation fuel to identify the enhanced trace compound therein; and
identifying a feedstock as a source for the fuel based on the identified trace compound.

18. The method of claim 17 further comprising determining that the fuel is biologically-sourced based on the identified trace compound.

19. The method of claim 17 further comprising correlating the identified trace compound to a fuel property effect of the fuel.

* * * * *